United States Patent [19]
Rivetti et al.

[11] Patent Number: 5,631,395
[45] Date of Patent: May 20, 1997

[54] METHOD FOR REMOVING THE ACIDIC IMPURITIES CONTAINED IN A VAPOURIZED STREAM COMPOSED BY ORGANIC VAPOURS AND WATER

[75] Inventors: Franco Rivetti, Milan; Daniele Delledonne, Oleggio, both of Italy

[73] Assignee: Enichem Synthesis S.p.A., Palermo, Italy

[21] Appl. No.: 456,073

[22] Filed: May 31, 1995

[30] Foreign Application Priority Data

Jun. 3, 1994 [IT] Italy .................... MI94A1159

[51] Int. Cl.$^6$ .................... C07C 69/96
[52] U.S. Cl. .................... 558/277
[58] Field of Search .................... 558/277

[56] References Cited

U.S. PATENT DOCUMENTS 4,218,391 8/1980 Romano et al. .
4,318,862 3/1982 Romano et al. .

OTHER PUBLICATIONS

Database WPI, Derwent Publications, AN 86–287960, JP–A–61210057, Sep. 18, 1986.

Primary Examiner—Johann Richter
Assistant Examiner—John Peabody
Attorney, Agent, or Firm—Oblon, Spivak, McClelland, Maier & Neustadt, P.C.

[57] ABSTRACT

Method for removing the acidic impurities contained in a vaporized stream consisting of an alkanol, an alkyl carbonate, water and still other organic species in minor amounts, which method consists in sending said stream to a solid adsorption reactor comprising alumina or activated charcoal.

17 Claims, 1 Drawing Sheet

METHOD FOR REMOVING THE ACIDIC IMPURITIES CONTAINED IN A VAPOURIZED STREAM COMPOSED BY ORGANIC VAPOURS AND WATER

The present invention relates to a method for removing the acidic impurities contained in a vaporized stream consisting of organic vapours and water.

More particularly, the present invention relates to a method for removing the acidic impurities contained in a vaporized stream consisting of an alkanol, an alkyl carbonate, water and still other organic species in minor amounts, which removal method consists in sending said stream to an adsorption reactor containing a solid adsorbent bed comprising alumina or activated charcoal.

A further object of the present invention is the application of said removal method to the removal of acidic impurities, more precisely hydrogen chloride, from a vaporized stream mainly containing methanol, dimethyl carbonate, water and minor amounts of other organic species, in a process for dimethyl carbonate synthesis.

Dimethyl carbonate ("DMC" herein in the following) is a widely used, very flexible chemical product which is used as such as solvent, or as a fuel additive; furthermore, DMC is an important intermediate product in the synthesis of other alkyl or aryl carbonates, useful as synthetic lubricants, solvents, monomers for polymeric materials and for preparing isocyanates, urethanes, ureas and polycarbonates.

The most widely used route for producing DMC presently is the one which is based on oxidative methanol carbonylation, in particular in the presence of CuCl as a catalyst, according to the reaction equation:

$$2\ CH_3OH + CO + \tfrac{1}{2}O_2 \rightarrow (CH_3O)_2CO + H_2O$$

The preparation of DMC according to such a reaction is disclosed, e.g., in commonly owned U.S. Pat. Nos. 4,218,391 and U.S. 4,318,862, and in European patent applications EP-A-460,732 and EP-A-460,735.

In the processes which are based on DMC preparation method as reported above, the separation of reaction effluent from catalyst is usually advantageously carried out by evaporation, by taking advantage of the difference in volatility between the organic products and water on the one hand (volatiles) and the components of the catalytic system (non-volatiles) on the other hand. In that way, vapour streams are obtained which typically contain (% by weight):

$CH_3OH$: from 45% to 70%;

DMC: from 25% to 50%;

$H_2O$: from 2% to 6%; and other organic byproducts: from 2% to 3%.

Unfortunately, the above said streams result to be contaminated by variable amounts of hydrogen chloride, because the halogen is an essential component of the catalytic system. According to the adopted working methods, such amounts can be usually comprised within the range of from 5 ppm to 600 ppm of hydrogen chloride, by weight, based on weight of vapours.

The presence of chloride ions causes considerable problems of technical-economic nature in the facility section downstream of the reactor, i.e., that section of the facility in which the product separation and purification operations are carried out.

In fact, the presence of hydrogen chloride causes very serious problems of equipment corrosion, with the need consequently arising for having resort to special, corrosion resistant material for building the separation and purification sections and with a considerable burden.

The removal of chloride ions contained in the vaporized phase effluent from dimethyl carbonate synthesis reactor would therefore allow the above disclosed drawbacks to be overcome.

According to the techniques known from the prior art, the removal of acidic impurities, in particular hydrogen chloride, contained in a stream of organic vapours, can only be carried out after condensing said stream, so as to obtain a liquid phase.

After obtaining the liquid phase, the removal of the acidic impurities, in particular hydrogen chloride, can be carried out by treating said liquid phase with an alkaline or basic agent, either in solid state, or in solution (neutralization). Unfortunately, in this case, a large number of problems arise which are associated with the precipitation of salts formed during the neutralization reaction in the operating facilities, with consequent fouling of the latter; with their separation from the process fluids and their end disposal to dump; with the decomposition of produced DMC induced by alkaline hydrolysis in case of feed of an excess amount of the alkaline or basic agent.

According to an alternative route, the liquid phase obtained from the condensation of the stream of organic vapours, can be caused to flow above a fixed bed constituted by ionic exchange resins of cationic type. Unfortunately, also in this case, problems arise from the absorbent power of ion exchange resins of cationic type which is generally rather low, it being comprised within the range of from 4 to 5 equivalents per kg of dry resin.

The present Applicant has now found a method which makes it possible the acidic impurities to be removed from a vaporized organic phase, by directly operating in the vapour phase, and thus avoiding the problem of condensation of the vaporized phase into a liquid phase, in a simple and advantageous way, by using solid adsorbent beds comprising alumina or activated charcoal. Such a method makes it possible the level of said acidic impurities to be reduced down to such values—anyway lower than 1 ppm—as to allow equipment made from traditional materials to be used, thus avoiding the problems connected with the use of the usual neutralization techniques as described above.

Although this type of solid adsorbants is normally used in order to remove acidic impurities from incondensible process gases such as, e.g., in dehydrochlorination of hydrogen coming from refinery "reforming", they were never used before for removing acidic impurities from organic vapours. On the contrary, it is surprising that such systems are effective in removing hydrogen chloride from organic vapours and water, because these should effectively compete with hydrogen chloride for the adsorption sites. In fact, such systems are normally used for adsorbing acidic impurities from incondensible gases (air, and so forth), as, e.g., disclosed in Ullmanns: "Encyklopädie der Technischen Chemie", Band 2, Volume 4, page 600.

The use of the method according to the present invention is all the more surprising when one considers that substantial water amounts (from 2% to 6% by weight) are present in the vaporized stream because water, in larger amounts than 0.1%–0.2% by weight, is known to inhibit adsorption of acids by alumina, because water competes with them for active centres.

Therefore, the object of the present invention is a method for removing the acidic impurities contained in a vaporized stream composed by an alkanol, an alkyl carbonate, water and other organic products in minor amounts, which method consists in sending said stream to an adsorption reactor containing a solid adsorbent bed comprising alumina or activated charcoal.

Solid adsorbent beds useful for the purpose of the present invention are also those comprising modified aluminas or modified activated charcoals.

Aluminas or modified aluminas useful for the purpose of the present invention are those which are available from the market, produced by Katalco (I.C.I.), ALCOA (Aluminum Company of America), La Roche Chemicals, Discovery Aluminas.

Specific examples of alumina or modified alumina grades useful for the purpose of the present invention are: PURASPEC® 2110, produced by Katalco, which is an alumina modified with sodium salts (sodium aluminate); A-203 Cl®, manufactured by La Roche Chemicals, which is a modified alumina with inorganic promoters; Cl-750®, produced by Discovery Aluminas, which is a modified alumina with inorganic salts; SELEXSORB® SPCL, produced by ALCOA, which is a modified alumina with inorganic promoters.

Activated charcoals or modified activated charcoals useful for the purpose of the present invention are those grades which are available from the market, produced by Calgon Carbon Corporation, American Norit, Degussa and Westvaco Corporation.

Specific examples of activated charcoals or modified activated charcoal grades useful for the purpose of the present invention are: CALGON Type IVP®, which is a modified activated charcoal impregnated with sodium hydroxide, produced by Calgon Carbon Corporation; DARCO®, which is an activated charcoal produced by American Norit.

According to the present invention, aluminas and activated charcoals are advantageously used in pellet form, with an average size of the pellets comprised within the range of from 2 mm to 4 mm of diameter.

The geometry of the adsorbent bed useful for the purpose of the present invention, is the usual geometry as used in industrial facilities for the absorption of acidic impurities from incondensible gases, or gas purification. For example, an adsorbent bed can be used which is contained in a reactor in which the ratio of reactor height to diameter is comprised within the range of from 3 to 20. Said adsorbent beds are capable of retaining amounts of hydrogen chloride of up to 10%–14%, based on their weight.

For the purpose of the present invention, the vaporized stream containing the acidic impurities such as, e.g., hydrogen chloride, is sent to the reactor containing the solid adsorbant.

The above said vaporized stream can possibly contain incondensible gases, such as, e.g., $H_2$, CO, $CO_2$ and $N_2$. In this case, the percent ratio of incondensible gases to condensible vapours is generally comprised within the range of from 0% to 90% by volume, preferably of from 0% to 70% by volume.

The temperature and pressure conditions under which the method is carried out, are not critical. In general, the reactor containing the solid adsorbent bed is kept at a temperature comprised within the range of from 30° C. to 150° C., preferably of from 50° C. to 110° C. and under a pressure comprised within the range of from 0.1 to 50 abs. atm, preferably of from 1 to 40 abs. atm, with the proviso that the selected pair of values should be such as to prevent the vapours from condensing under the selected operating conditions.

The contact times are advantageously comprised within the range of from 0.3 to 30 seconds (as calculated under standard conditions), to which values of GHSV (Gas Hourly Space Velocity) correspond which are comprised within the range of from 12000 to 120 hours$^{-1}$, more preferably with contact times comprised within the range of from 0.6 to 18 seconds, to which GHSV values correspond which are comprised within the range of from 6000 to 200 hours$^{-1}$.

Necessary condition for method applicability is the chemical inertness of vaporized substrates versus the adsorbant. In this case, the removal of any types of acidic impurities from any types of organics streams, also containing water, can be carried out by using the method according to the present invention.

According to an embodiment of the present invention, the above said method can be used in order to remove the acidic impurities from vaporized streams containing methanol, dimethyl carbonate, water and still other organic species in minor amounts.

Preferred vaporized streams for the purpose of the present invention are those having the following composition (% by weight):

$CH_3OH$: from 45% to 70%;

DMC: from 25% to 50%;

HCl: from 5 to 1000 ppm;

$H_2O$: from 2% to 6%; and other organic byproducts: from 2% to 3%.

The method according to the present invention makes it possible the acidic impurities to be removed down to lower levels than 1 ppm by weight.

In the case when the method according to the present invention is applied to DMC synthesis process, the process stream sent as feed to the product (DMC) purification/ separation section results to be free from hydrogen chloride, with the consequent considerable advantage that for building said section, normal materials can be used without any corrosion problems and financial burdens.

In order to better understand the present invention and to practice it, some illustrative examples are reported in the following, which shall not be construed as being in anyway limitative of the purview of the same invention.

EXAMPLE 1

Figure 1:
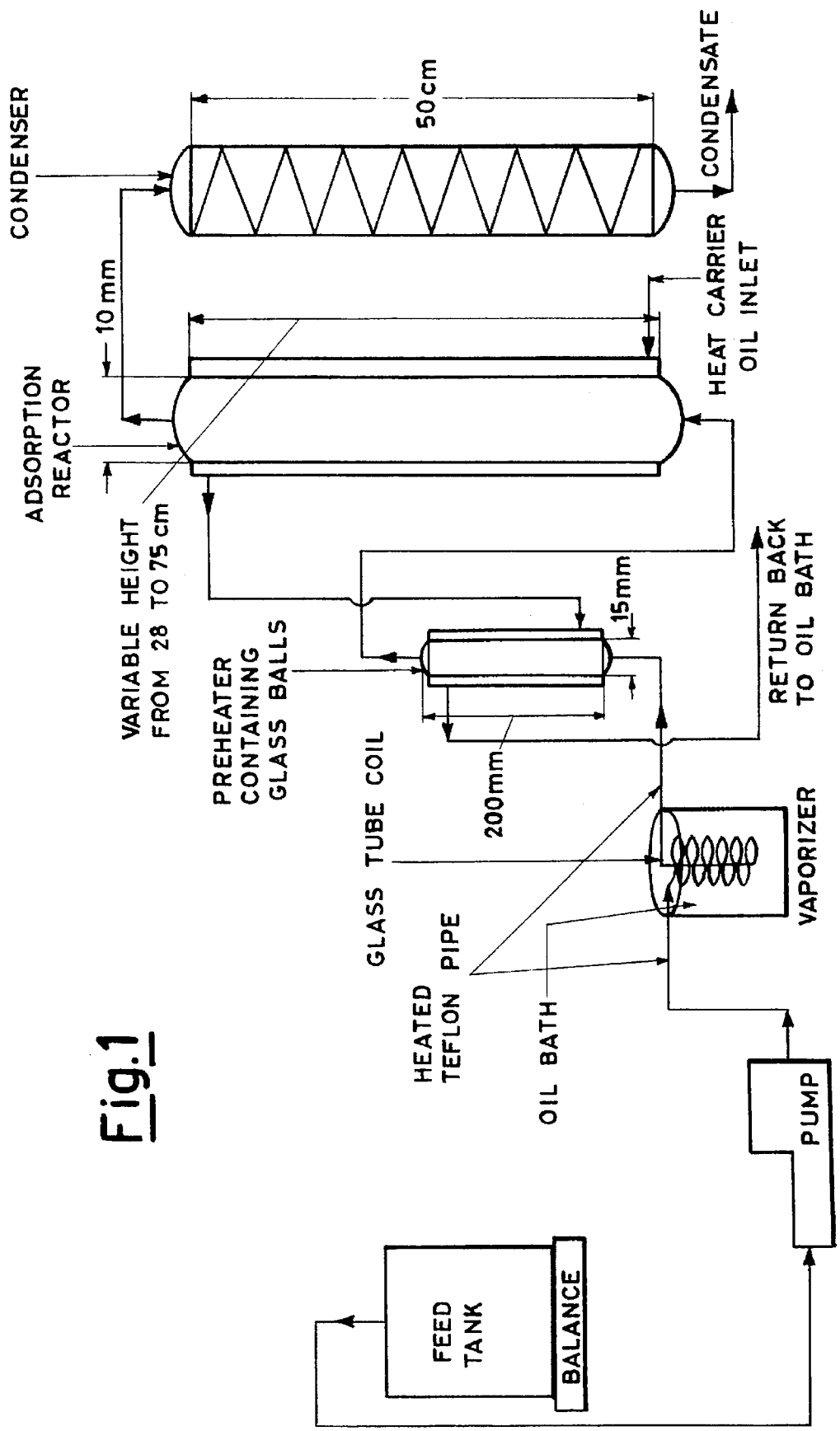
FIG. 1 describes an apparatus used in examples.

The apparatus used in this example is illustrated in FIG. 1.

Said apparatus is constituted by a peristaltic pump which delivers the feed stream to a vaporizer constituted by a glass tube coil immersed in an oil bath which is at a suitable temperature for vaporizing all feed, a preheater, the adsorption reactor containing alumina or activated charcoal, and finally a condenser with its relevant condensate collecting flask.

All lines connecting the several equipment pieces are of glass or teflon and are heated with an electrical heating band, so as to prevent the feed stream from getting condensed at cold spots.

The alumina containing reactor has a diameter of 15 mm and a variable height, ranging from 28 to 75 cm, as a function of the amount of adsorbant which one wishes to charge to it.

In Table 1, the results are reported which were obtained as a function of the used types of alumina or activated charcoal; the contact times, expressed as GHSV (h$^{-1}$); the temperature of alumina or activated charcoal containing adsorption reactor.

TABLE 1

| Adsorbant type | GHSV, h$^{-1}$ | Reactor temperature, °C. | Chlorine ions contained in the condensate ppm |
| --- | --- | --- | --- |
| PURASPEC ® 2110 alumina, | 5700 | 110 | <1 |
| 5 × 8 mesh | 4800 | 110 | <1 |
|  | 5700 | 90 | <1 |
|  | 2800 | 80 | <1 |
|  | 1000 | 80 | <1 |
| A-203 Cl ® alumina, | 3000 | 95 | <1 |
| 5 × 8 mesh | 1000 | 85 | <1 |
| SELEXSORB ® spcl ALUMINA, | 1300 | 85 | <1 |
| ⅛" | 900 | 85 | <1 |
| Cl-750 ® alumina, | 1000 | 90 | <1 |
| 5 × 8 mesh | 1000 | 80 | <1 |
| CALGON TYPE IVP ® activated charcoal 4 × 5 mesh | 1200 | 80 | <1 |
| DARCO ® activated charcoal, 20–40 mesh | 1000 | 80 | <1 |

Feed (% by weight):

$H_2O$: 5%;

$CH_3OH$: 60%;

DMC: 35%; and

HCl: 5 ppm.

EXAMPLE 2

This example discloses a typical test of adsorption of hydrogen chloride contained in a vaporized feed which is caused to flow above an alumina or activated charcoal bed. The apparatus used for this purpose is the same apparatus as used in Example 1, shown in FIG. 1.

The adsorption reactor is filled with PURASPEC® 2110 alumina in form of pellets of 5×8 mesh (42 ml, 34.3 g), and the reactor temperature is set at 80° C., the temperature of the vaporizer is set at 100° C. and the preheater temperature is set at 80° C.

To the vaporizer, a stream of 210.4 g/h is fed (GHSV of about 2800 h$^{-1}$) of a solution having the following composition (% by weight):

$H_2O$: 4.78%;

$CH_3OH$: 60.41%;

DMC: 34.82%; and

HCl: 5 ppm;

and 210 g/h of condensate is collected, having the following composition (% by weight):

$H_2O$: 4.68%;

$CH_3OH$: 60.8%;

DMC: 34.52%; and

HCl: <1 ppm.

The test is continued for longer than 50 hours and the adsorption of hydrogen chloride was always complete. Measurements of condensate conductivity yielded values comprised within the range of from 0.15 µS to 0.3 µS throughout the test time.

EXAMPLE 3

The same apparatus is used as disclosed in Example 1.

In this case the feed has the following composition (% by weight):

$H_2O$: 5%;

$CH_3OH$: 60%;

DMC: 35%; and

HCl: 500 ppm.

The purpose of this example is of verifying the adsorption degree supplied by aluminas and activated charcoals listed in following Table 2, as a function of the contact time (GHSV), with the amounts of adsorbed hydrogen chloride being expressed as % by weight based on weight on charged adsorbant.

The test results are reported in Table 2. Such results clearly demonstrate that, although the concentration of hydrogen chloride was increased up to 500 ppm, all tested alumina and activated charcoal grades completely adsorb the acid the concentration of which, in fact, remains constantly lower than 1 ppm in the condensates, until the adsorbed amounts are reached which are reported in Table 2.

TABLE 2

| Adsorbant type | GHSV, h$^{-1}$ | Reactor temperature, °C. | Adsorbed HCl %, based on adsorbant charged to column |
| --- | --- | --- | --- |
| PURASPEC ® 2110 alumina, | 3000 | 95 | 3.8 |
| 5 × 8 mesh | 1200 | 80 | 10.0 |
| A-203 Cl ® alumina, | 2500 | 85 | 4.15 |
| 5 × 8 mesh | 3000 | 80 | 12.50 |
| Cl-750 ® alumina, | 1200 | 80 | 11 |
| 5 × 8 mesh |  |  |  |
| CALGON TYPE IVP ® activated charcoal 4 × 5 mesh | 700 | 88 | 6.5 |

We claim:

1. A method for removing acidic impurities, comprising the steps of:

contacting a vaporized stream comprising an alkanol, an alkylcarbonate, water, and acidic impurities in an adsorption reactor comprising a solid adsorbent bed, wherein said adsorbent bed comprises an adsorbent selected from the group consisting of alumina, activated charcoal, and a mixture thereof.

2. The method of claim 1, wherein said alumina is a modified alumina.

3. The method of claim 2, wherein said modified alumina is an alumina modified with a modifier selected from the group consisting of an inorganic promoter, a sodium salt, and an inorganic salt.

4. The method of claim 1, wherein said activated charcoal is a modified activated charcoal.

5. The method of claim 4, wherein said modified activated charcoal is an activated charcoal modified with sodium hydroxide.

6. Method of claim 1 wherein said adsorbent is in pellet form, and wherein the average diameter of said pellets is 2 mm to 4 mm.

7. Method of claim 1 wherein a ratio of the height of said reactor to the diameter of said reactor is 3 to 20.

8. Method of claim 1 wherein said reactor is maintained at a temperature of 30°–150° C. and a pressure of 0.1–50 atmospheres.

9. Method of claim 8 wherein said temperature is 50°–110° C.; and wherein said pressure is 1–40 atmospheres.

10. Method of claim 1 wherein said vaporized stream comprises methanol, dimethylcarbonate, water and HCl.

11. Method of claim 1 wherein said acidic impurities comprise HCl.

12. Method of claim 10, wherein a concentration of a methanol is 45–70% by weight of said vaporized stream; the concentration of dimethylcarbonate is 25–50% by weight of said vaporized stream; a concentration of HCl is 5–100 parts per million of said vaporized stream; and wherein a concentration of water is 2–6% by weight of said vaporized stream.

13. The method of claim 1 wherein a concentration of acidic impurities is reduced to less than 1 ppm by weight of said vaporized stream, after said contacting step.

14. The method of claim 10, wherein concentration of HCl is reduced to less than 1 ppm by weight of said vaporized stream, after said contacting step.

15. The method of claim 1 wherein said vaporized stream further comprises at least one gas selected from the group consisting of $H_2$, CO, $CO_2$ and $N_2$; and wherein the percent ratio of a volume of said gas to a volume of said alkanol, and alkyl carbonates and water is 0–90%.

16. The method of claim 1 wherein said contacting step comprises a time range of 0.3–30 seconds; and wherein said contacting step comprises a Gas Hourly Space Velocity value within the range of 12,000–120 $hour^{-1}$.

17. The method of claim 1 wherein said adsorbent bed adsorbs 10–14% of HCl, by weight of said adsorbent bed.

* * * * *